United States Patent [19]

Trafton et al.

[11] 3,973,912
[45] Aug. 10, 1976

[54] MICRO-GASOMETRIC METHOD AND APPARATUS

[75] Inventors: John E. Trafton, Woodbury, N.J.; Philip E. Nichols, Ridley Park, Pa.; Royce Haynes, Sewell, N.J.

[73] Assignee: American Hospital Supply Corporation, Evanston, Ill.

[22] Filed: June 2, 1975

[21] Appl. No.: 582,680

[52] U.S. Cl. .............................. 23/230 B; 23/253 R
[51] Int. Cl.[2] .................. G01N 7/00; G01N 31/20; G01N 33/16
[58] Field of Search .............. 23/230 B, 253 R, 259

[56] References Cited
UNITED STATES PATENTS

| | | | |
|---|---|---|---|
| 2,680,060 | 6/1954 | Natelson | 23/230 B X |
| 2,974,018 | 3/1961 | McNeilly | 23/253 R |
| 3,639,830 | 2/1972 | Harnoncourt | 23/230 B X |
| 3,756,782 | 9/1973 | Phillips | 23/230 B |

*Primary Examiner*—Robert M. Reese
*Attorney, Agent, or Firm*—Dawson, Tilton, Fallon & Lungmus

[57] ABSTRACT

A method and apparatus for determining the carbon dioxide content of micro samples of blood, serum, or other body fluid. In performing the method, a micro quantity of sample is introduced into one compartment of a double-compartmented open-topped reaction vessel, the other compartment containing a reagent capable of liberating the carbon dioxide from the sample when the two are mixed. The open top of the vessel is then sealed so that its interior communicates only with a capillary gasometer, and the contents of the vessel are then thoroughly mixed. The volume of evolved gas is measured directly from the graduated capillary gasometer by observing the extent of displacement of an indicating liquid therein. The structure of the device is described, along with the structure and method for adjusting the volume of the reaction vessel, after sealing and before mixing, to locate the meniscus of the liquid in the capillary at a selected starting point.

16 Claims, 6 Drawing Figures

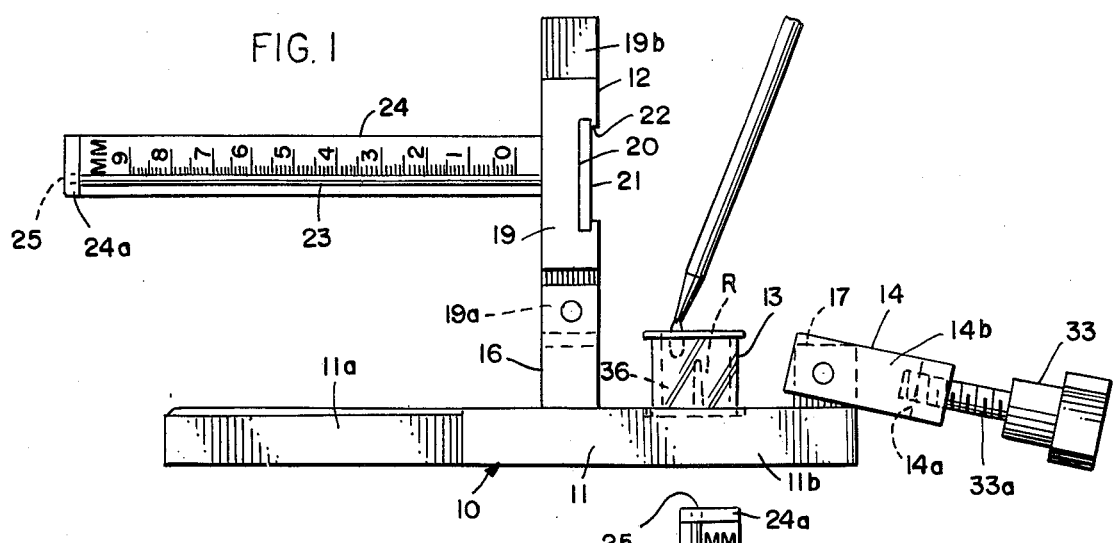
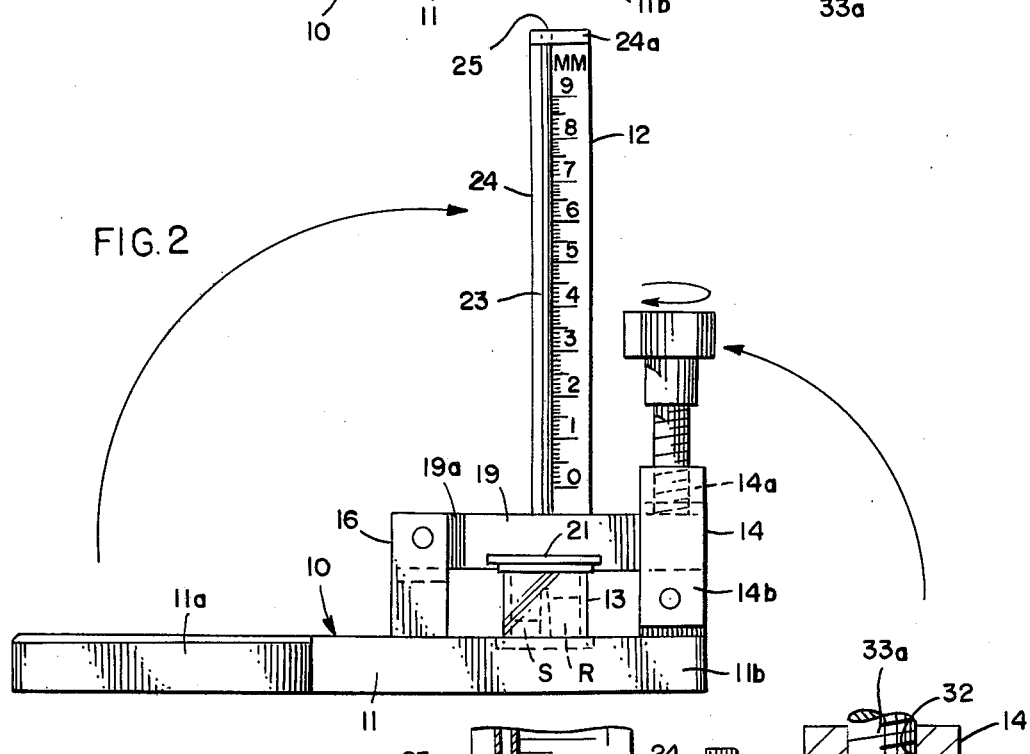
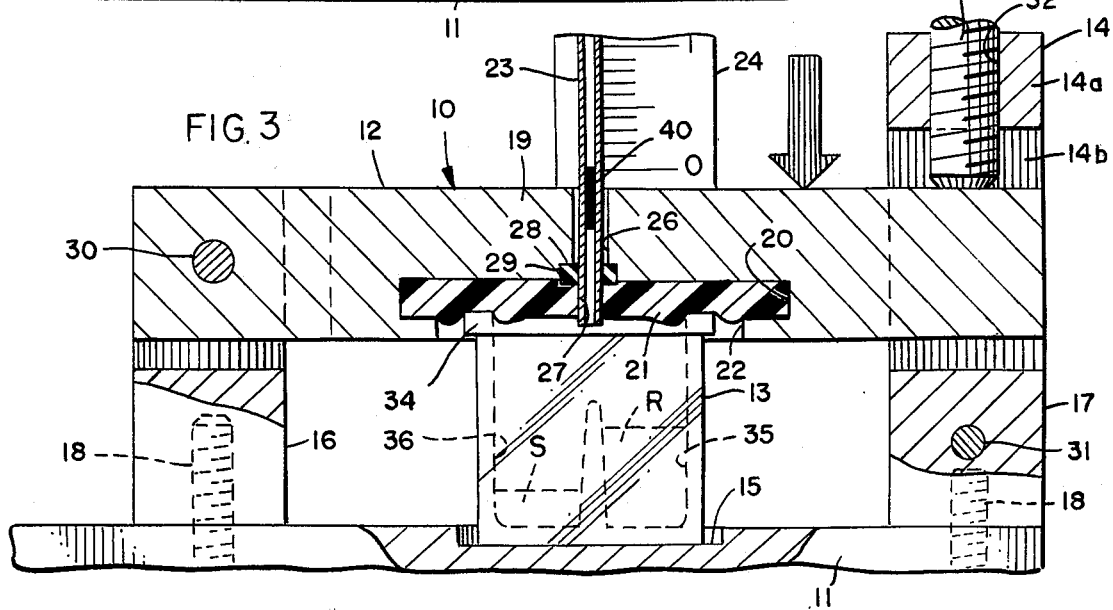

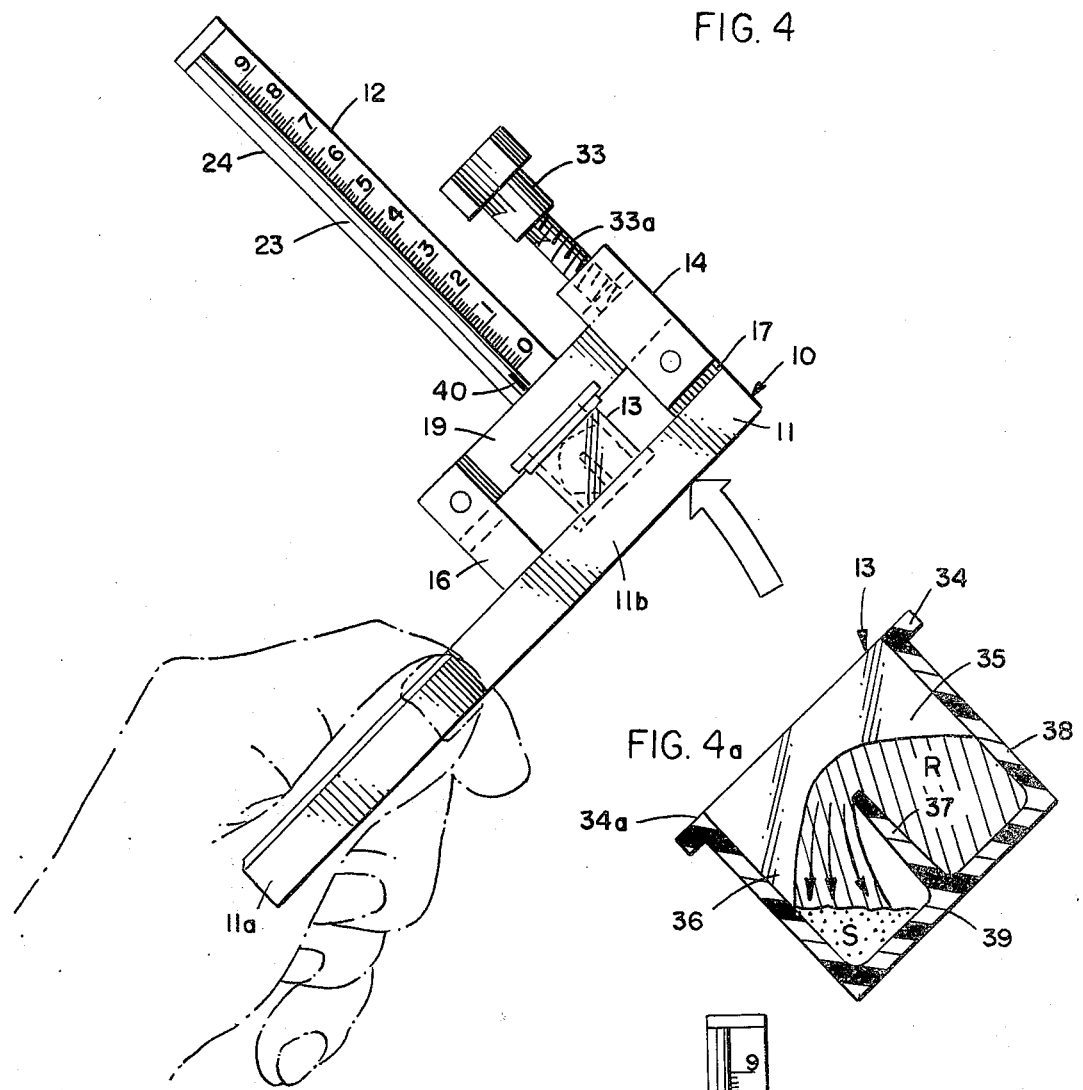
FIG. 4
FIG. 4a
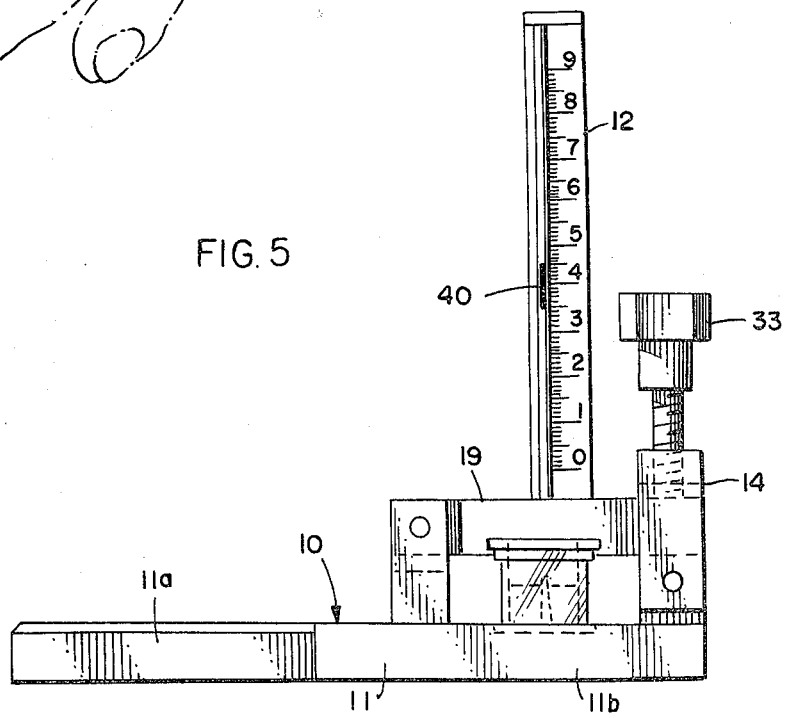
FIG. 5

MICRO-GASOMETRIC METHOD AND APPARATUS

BACKGROUND

U.S. Pat. No. 3,756,782 discloses a method and apparatus for determining the carbon dioxide content of a blood sample in which an acid-containing syringe is coupled in gas-tight relation to a vial containing a blood sample. The acid is injected into the vial and the sample, upon such acidification, releases carbon dioxide which may be quantitatively measured by the extent of displacement of the syringe plunger. As brought out in that patent, such a system is based on the classical Van Slyke procedure but, unlike prior systems used in the clinical laboratory, is relatively uncomplicated in structure and operation. The system of U.S. Pat. No. 3,756,782 does have a shortcoming; however, it is not well suited for determining the carbon dioxide content of micro samples (i.e., under 0.5 milliliters) of biological fluid.

Equipment for measuring the carbon dioxide content in micro samples is known, as disclosed, for example, in U.S. Pat. No. 2,680,060. The disadvantages of available micro-gasometers have already been indicated; in general, they are bulky, expensive, and complex in both structure and operation. It will be readily appreciated that operative complexities are particularly undesirable, not simply because they consume time and cause delays, but because they increase the risk of manipulative error which, in any diagnostic procedure, may have most serious consequences. Also, because such devices are sometimes provided with mercury-containing tubes to measure pressure, they present additional risks which attend the use of a hazardous substance.

SUMMARY

This invention is directed to a system for measuring carbon dioxide in biological fluids which is simple and reliable in operation and construction, and which is particularly suited for the processing of micro samples of such fluids. For purposes of this disclosure, the term "micro" refers to sample volumes less than 0.5 milliliters and includes volumes which may even be small enough to fall within what is commonly designated the ultra-micro range (i.e., less than 0.05 milliliters). The method and apparatus of this invention are therefore well suited for use in measuring the carbon dioxide content of blood (including serum or plasma) taken from pediatric patients and other subjects from whom the taking of larger samples might have undesirable effects.

One aspect of this invention lies in the discovery that the carbon dioxide content of a sample of biological fluid may be effectively and readily determined by utilizing a two-compartmented reaction vessel in a gas-tight system, the reaction vessel being in direct communication with an open-topped transparent capillary tube containing an indicating liquid. The separate compartments contain measured quantities of the body fluid and a gas-liberating reagent and, on mixing of the fluid and reagent, carbon dioxide is liberated from the sample to cause the indicating liquid in the manometer to be displaced a distance proportional to the volume of liberated gas.

The apparatus includes a base for supporting the reaction vessel, a gasometer head assembly which is movably mounted upon the base and which may be shifted into sealing engagement with the open top of the vessel, and adjustable clamping means for holding the head assembly and vessel in sealing engagement and, at the same time, permitting small selective adjustments in the volume of the sealed vessel. Such volume adjustments are possible because of a resilient gasket interposed between the plate or cover member of the head assembly and the mouth of the open-topped vessel, and the effect of such adjustments is to permit zeroing of the liquid in the gasometer after the reaction vessel has been sealed and before the reactants have been mixed.

In the disclosed embodiment of the invention, the reaction vessel is transparent (or at least translucent) and has its compartments arranged in side-by-side relation, divided by an upstanding partition which is lower than the full height of the vessel. The perimetric upper edge or mouth of the open-topped vessel extends along a single plane and is adapted to make sealing contact with the gasket carried by the gasometer head assembly. Where replacability of the capillary tube is desired, a second gasket may be provided to insure a gas-tight sealing engagement between the capillary tube and the remainder of the gasometer head.

The size of the base and head are such that the entire apparatus is easily lifted, tipped, and moved about to cause the gas-liberating reagent to flow into the sample compartment and to insure complete mixing of the reactants in the vessel. For that purpose, the base is equipped with an extension which serves as a convenient handle for manipulation of the apparatus.

Other advantages and objects of this invention will become apparent from the specification and drawings.

DRAWINGS

FIG. 1 is a side elevational view of a micro-gasometer embodying the invention, the apparatus being illustrated in opened condition at the commencement of a sample-testing procedure.

FIG. 2 is a side elevational view similar to FIG. 1 but showing the apparatus in closed condition in a subsequent step of the operative procedure.

FIG. 3 is an enlarged vertical sectional view showing the relationship between the reaction vessel and the remainder of the apparatus after the resilient gasket has been compressed to adjust the meniscus of the indicating liquid of the gasometer.

FIG. 4 is a side elevational view illustrating a further step in the operation of the apparatus.

FIG. 4a is an enlarged vertical sectional view of the reaction vessel illustrating somewhat schematically the intermixing of the reactants when the apparatus is tipped in the manner depicted in FIG. 4.

FIG. 5 is a side elevational view illustrating the condition of the apparatus upon the completion of the gas-liberating reaction.

DESCRIPTION

Referring to the drawings, the numeral 10 generally designates a micro-gasometer embodying this invention and comprising a base 11, a gasometer head assembly 12, a reaction vessel 13, and adjustable clamping means 14.

Base 11 is rigid, paddle shaped, and provided with a relatively narrow handle portion 11a which is dimensioned to fit comfortably within a user's hand (FIG. 4). While it should be understood that the dimensions might be varied considerably, effective results have been achieved with a base having maximum width and length dimensions of about 2.0 and 6.6 inches, respectively, and including a handle portion with width and length dimensions of about 1.3 and 2.4 inches, respectively.

The upper surface of the base's main body portion 11b is provided with a well or depression 15 for receiving and locating the lower end of the removable and disposable reaction vessel 13. Spaced from the well, on opposite sides thereof, are a pair of upstanding pivot blocks 16 and 17 which may be formed integrally with the base or, as in the illustration given, be formed as separate parts secured rigidly to the base by screws 18 or other fastening elements (FIG. 3).

The gasometer head assembly 12 is pivotally secured to upstanding block 16 and may be shifted between the open or releasing position of FIG. 1 and the lowered or vessel-engaging position of FIGS. 2 and 3. The head assembly comprises a generally rectangular plate member 19 having tongue portions 19a and 19b at opposite ends thereof and having a transverse slot 20 which extends from one side to the other and which receives a resilient contact member or gasket 21. As shown, the gasket is exposed from the underside of the plate member through an enlarged opening 22 which has dimensions substantially greater than the top dimensions of vessel 13 (FIG. 3).

The gasometer head assembly 12 also includes capillary tube 23 and capillary tube support 24. The support is rigidly fixed to plate member 19 and projects upwardly when the plate member is in its lowered or closed position (FIG. 2). At its extreme upper or distal end, the support is provided with a transversely-projecting arm 24a which is apertured at 25 (FIG. 2) to receive the upper end of the capillary tube 23. The lower end of the tube extends through bore 26 in plate member 19 and through opening 27 in gasket 21. To achieve a fluid-tight seal between the outer surface of the capillary tube and plate 19, the plate is counter-bored at 28 to receive sealing ring 29. The sealing ring fits snugly about the outer surface of the capillary tube and sealingly engages the plate member 19 when the parts are assembled as illustrated in FIG. 3. The capillary gasometer 23, which may take the form of a standard glass laboratory capillary tube of, for example, 100 microliter capacity, is therefore supported at its open upper and lower ends, the upper end being received in opening 25 and the lower end being held frictionally in place by sealing ring 29 which is in turn locked against axial displacement (and sealingly engaged) by gasket 21. It will be observed that the capillary tube locks the gasket against axial movement and that removal of the gasket first requires the capillary tube to be lifted (with a force sufficient to overcome the frictional resistance of ring 29) until the extreme lower end of the tube is disposed above the gasket. It will also be noted that the capillary tube is graduated, the graduation scale preferably being imprinted or otherwise applied to the tube support 24. The scale is conveniently graduated in millimeters although any other appropriate measurement system may be utilized.

Tongue portion 19a of plate 19 is pivotally connected by transverse pin 30 to pivot block 16. For that purpose, the pivot block 16 may be formed in the shape of a clevis, having a pair of upstanding arms 16a which define a space therebetween for receiving tongue portion 19a.

Clamp 14 also takes the shape of a clevis, having a transverse connecting portion 14a and a pair of depending side portions 14b which straddle pivot block 17 and which are pivotally connected to the block by transverse pin 31. The transverse connecting portion 14a is provided with a threaded opening 32 which receives the threaded shank 33a of a knob-equipped adjustment member 33. As shown most clearly in FIGS. 2 and 3, the dimensions of the space between the side arms 14b of the clamp, and between the connecting portion 14a of the clamp and pivot block 17, are larger than the corresponding dimensions of the tongue portion 19b at the free end of plate member 19. The difference in the vertical dimensions is particularly significant because it permits limited pivotal (essentially vertical) adjustment of the plate member 19, by means of rotating the knob-equipped adjustment member 33, after a reaction vessel 13 has been clamped in position between base 11 and manometer head 12.

The reaction vessel is generally rectangular in side elevation and in horizontal section, although other configurations might be acceptable. It is important, however, that the vessel be open topped, having an upper rim 34 providing an upper surface 34a lying along a single plane. The interior of the vessel is divided into two compartments 35 and 36 by a transverse partition or septum 37. It will be noted that the partition extends transversely relative to the elongated base 11 and that it is substantially lower than the side walls 38 of the reaction vessel. The bottom surface 39 of the vessel lies along a plane parallel with the one defined by top surface 34a; therefore, the vessel may be securely and sealingly clamped between the gasometer head and base in the manner illustrated.

The capillary tube of the manometer head contains a small quantity of any suitable liquid 40 that would be visible through the transparent wall of the tube. Any non-toxic aqueous dye solution may be used, the solution preferably containing a surfactant (such as Triton X-100, marketed by Rohm & Haas Company, Philadelphia, Pennsylvania) to insure free or unrestrained movement of the dye solution within the capillary passage. While the non-aqueous liquids might be used, they should have a specific gravity not appreciably greater than water to avoid or reduce the possibility that such liquids might escape from the open-ended tube.

In carrying out the method of the invention, a reaction vessel 13, having one of its compartments 35 nearly filled with a gas-liberating reagent R, is located in well 15 of base 11 as illustrated in FIG. 1. The reagent may be an acid such as lactic acid (22 percent) as disclosed in U.S. Pat. No. 3,756,782. The amount of reagent in compartment 35 should be as close as possible to the capacity of that compartment without risking unintentional spilling of the reagent into adjacent compartment 36 during normal handling of the vessel and the apparatus as a whole. Thus, if the capacity of compartment 35 (measured to the top of septum 37) is 0.6 milliliters, it has been found that such a compartment may conveniently receive 0.5 milliliters of reagent.

A measured quantity of biological fluid (blood, serum, or plasma) is pipetted into adjacent compartment 36 (FIG. 1). The amount depends partly on the volume of reagent R in the adjacent compartment, it being essential that the reagent be present in substantial excess. Therefore, if compartment 35 contains 0.5 ml reagent (lactic acid), 100 microliters (0.1 milliliters) of sample S may be placed on compartment 36.

The gasometer head 12 is then shifted into its closed position, and clamping means 14 is manipulated, to seal the open top of the reaction vessel so that it communicates only with the lower end of the capillary tube 23. Attention is directed to the fact that the body of indicator liquid 40 in the capillary tube will assume a position at the tube's extreme lower end when the tube is supported vertically (the surfactant contributing in preventing the liquid from sticking in an elevated position), but that as resilient gasket or cushion 21 is compressed following initial sealing contact between the gasket and the vessel, liquid 40 is forced upwardly within the capillary tube because of the reduction in the total volume of the vessel's interior (FIG. 3). Therefore, in operation of the apparatus, knob 33 of the clamping means is simply rotated to compress gasket 21 until a meniscus of liquid 40 (preferably the upper meniscus) has reached a selected starting point (zero) on the scale.

A modified operating procedure is to tighten the clamping means until the meniscus is slightly above the desired starting level (zero) and then reverse rotation of the knob, thereby relieving the compressive force, until the meniscus has dropped to the zero point. Such a technique may be of value in minimizing drift in the operation of the manometer resulting from creep or flow of the material of the resilient gasket.

With the meniscus stabilized at the zero level, the operator simply lifts the entire apparatus, gripping it by handle 11a, and tips it so that the gas-liberating reagent flows from compartment 35 into compartment 36 (FIGS. 4 and 4a). Since the reagent is present in substantial excess, compartment 35 need not be emptied to produce complete reaction. Since tipping of the apparatus may be most easily accomplished by raising the clamp-equipped end of the base (or lowering the handle end), it is apparent that in positioning the reaction vessel on the base in the initial step (FIG. 1) the compartment 35 which contains the reagent R should be located a greater distance from the handle than the sample-receiving compartment 36. Still holding the apparatus by its handle 11a, the operator repetitiously moves the apparatus about any and/or all of its axes to agitate the reactants. Such agitation should continue in a uniform manner for a measured interval such as, for example, 30 seconds. Thereafter, the level of the meniscus of liquid 40 is simply read from the scale of the gasometer head.

The procedure is repeated with a standard solution of known carbon dioxide content substituted for the sample of biological fluid, and the true carbon dioxide content of the sample is then calculated by the formula set forth in U.S. Pat. No. 3,756,782.

While in the foregoing, an embodiment of the invention has been disclosed in considerable detail for purposes of illustration, it will be understood by those skilled in the art that many of these details may be varied without departing from the spirit and scope of the invention.

We claim:

1. A method of measuring the carbon dioxide content of a biological fluid, comprising the steps of introducing a measured sample of biological fluid into one portion of an open-topped reaction vessel containing in another portion thereof a reagent capable of liberating the carbon dioxide content of said biological fluid upon admixture therewith, then sealing said vessel so that the interior thereof communicates only with the lower end of a graduated transparent capillary tube containing an indicator liquid defining a meniscus visible through the wall of said tube, then adjusting the volume of the interior of said vessel to shift said indicator liquid in said tube until said meniscus is at a selected position along said graduated capillary tube, and thereafter mixing the contents of said reaction vessel while the same communicates only with said capillary tube to measure the amount of carbon dioxide liberated by observing the extent of displacement of said indicator liquid in said tube.

2. The method of claim 1 in which said mixing step is performed by tipping said vessel and the capillary tube sealed thereto.

3. The method of claim 2 in which said sample and reagent are supported in separate adjacent compartments of said reaction vessel, said mixing step including the tipping of said vessel so that at least a substantial portion of said reagent flows from its compartment into the adjacent sample-containing compartment.

4. The method of claim 1 in which said sealing step includes securing a closure member upon the open top of said vessel with a resilient gasket interposed therebetween, said adjusting step comprising the incremental pressing of said gasket until the volume of said vessel is reduced sufficiently to raise the meniscus of said indicator liquid to said selected position along said tube.

5. The method of claim 4 in which said adjusting step includes preliminary compressing said gasket until said meniscus is displaced to a level slightly above said selected position, and thereafter reducing the compression of said gasket to lower the level of said meniscus to said selected position.

6. A device for measuring the carbon dioxide content of a biological fluid comprising a base adapted to support a reaction vessel, an open-topped reaction vessel removably supported upon said base, a gasometer head mounted upon said base for movement between a raised position spaced from said reaction vessel and a lowered position in sealing engagement with the open top thereof, said head including a transparent capillary gasometer tube, said tube communicating at its lower end with the interior of said reaction vessel when said head is lowered and containing an indicator liquid normally disposed at the tube's lower end, and clamping means for releasably securing said head in sealing engagement with said vessel and for altering slightly the position of said head when lowered to alter the volume of said vessel and thereby adjust the position of said liquid in said tube to a selected reference point.

7. The device of claim 6 in which said manometer head includes a plate member having an opening extending therethrough, said capillary tube having its lower end removably received in said opening of said plate member, and resilient sealing means engaging both said plate member and said capillary tube to form an air tight friction seal therebetween.

8. The device of claim 6 in which said base is provided with an elongated handle extension dimensioned to be receivable within the hand of an operator.

9. The device of claim 6 in which said base includes a well registrable with said gasometer head when the same is in its lowered position, said well receiving the lower end of said reaction vessel.

10. The device of claim 6 in which said head includes a resilient gasket engagable with the open top of said reaction vessel when said head is lowered, said gasket being compressible upon manipulation of said clamping means to reduce the sealed volume of said vessel and thereby alter the position of the indicator liquid within said capillary tube.

11. The device of claim 10 in which said clamping means includes a screw member equipped with a knob and engagable with said plate member for urging said plate member into sealing engagement with said vessel.

12. The device of claim 11 in which said plate member is hingedly connected to said base, said plate member having a resilient gasket along the undersurface thereof for engaging the open top of said vessel, said gasket being compressible upon adjustment of said screw member to reduce the volume of the interior of the vessel when sealed and thereby adjust the position of the indicator liquid in said tube to a selected reference point.

13. The device of claim 6 in which said open-topped reaction vessel is provided with a generally vertical partition dividing the interior of said vessel into two adjacent compartments, said partition having an upper edge spaced below the open top of said vessel.

14. The device of claim 13 in which said vessel has a base wall and in which the open top of said vessel is defined by a surface extending along a plane substantially parallel with said base wall.

15. The device of claim 14 in which said vessel has generally rectangular side walls.

16. The device of claim 14 in which said vessel is formed of transparent material.

* * * * *